(12) United States Patent
Inouye et al.

(10) Patent No.: US 7,396,655 B2
(45) Date of Patent: Jul. 8, 2008

(54) METHOD FOR ENHANCING ACTIVITY OF LUCIFERASE WITH FLUORESCENCE ACTIVITY

(75) Inventors: Satoshi Inouye, Kanagawa (JP); Satoko Sasaki, Kanagawa (JP)

(73) Assignee: Chisso Corporation, Osaka (JP)

( * ) Notice: Subject to any disclaimer, the term of this patent is extended or adjusted under 35 U.S.C. 154(b) by 0 days.

(21) Appl. No.: 11/393,233

(22) Filed: Mar. 30, 2006

(65) Prior Publication Data

US 2006/0234324 A1  Oct. 19, 2006

(30) Foreign Application Priority Data

Mar. 30, 2005  (JP)  ............................. 2005-099244

(51) Int. Cl.
  *C12Q 1/66*  (2006.01)
(52) U.S. Cl. ......................................................... 435/8
(58) Field of Classification Search .................. None
  See application file for complete search history.

(56) References Cited

U.S. PATENT DOCUMENTS

| | | | |
|---|---|---|---|
| 5,360,728 A | 11/1994 | Prasher | |
| 5,824,472 A | 10/1998 | Betlach et al. | |
| 2004/0235078 A1 | 11/2004 | Rosen et al. | |
| 2005/0054838 A1 | 3/2005 | Otsuka et al. | |

FOREIGN PATENT DOCUMENTS

| | | |
|---|---|---|
| EP | 1 666 488 A1 | 6/2006 |
| EP | 1 666 488 A1 | 7/2006 |
| JP | 61-135586 A | 6/1986 |
| JP | 1-132397 A | 5/1989 |
| JP | 3162480 A | 7/1991 |
| JP | 3167288 A | 7/1991 |
| JP | 2001-270899 A | 10/2001 |
| JP | 2004-035449 A | 2/2004 |
| JP | 2004-156017 A | 3/2004 |
| JP | 2006055082 | 3/2006 |
| WO | WO 87/05937 A1 | 10/1987 |
| WO | WO 00/29603 A3 | 5/2000 |
| WO | WO 03/054163 A3 | 7/2003 |
| WO | WO 03/060063 A3 | 7/2003 |
| WO | WO 03/082904 A3 | 10/2003 |
| WO | WO2005/014633 A1 | 2/2005 |

OTHER PUBLICATIONS

Huang et al. Identification and Characterization of a Catalytic Base in Bacterial Luciferase by Chemical Rescue of a Dark Mutant; Biochemistry, vol. 36, No. 48 (1997) pp. 14609-14615.*
Inouye et al. Imidazole-Assisted Catalysis of Luminescence Reaction in Blue Fluorescent Protein From the Photoprotein Aequorin; Biochemical and Biophysical Research Communications, vol. 354 (2007) pp. 650-655.*

Tsuji et al. "Bioluminescence Reaction Catalyzed by Membrane-Bound Luciferase in the 'Firefly Squid,' Watasenia Scintillans," *Biochimica et Biophsica Acta* 1564: 189-197 (2002).
Deng et al., "Crystal Structure of a Ca2+ -discharged Photoprotein," *J. Biological Chemistry*, 279 (32): 33647-33652 (Aug. 6, 2004).
Inouye, "Fusions to Imidazopyrazinone-Type Luciferases and Aequorin as Reporters," *Methods in Enzymology*, 326: 165-174 (2000).
Shimomura et al., "The relative rate of aequorin regeneration from apoaequorin and coelenterazine analogues," *Biochem J.*, 296: 549-551 (1993).
Shimomura et al., "Recombinant aequorin and recombinant semi-synthetic aequorins," *Biochem J.*, 270: 309-312 (1990).
Shimomura et al., "Light-emitting properties of recombinant semi-synthetic aequorins and recombinant fluorescein-conjugated aequorin for measuring cellular calcium," *Cell Calcium*, 14: 373-378 (1993).
Vysotski et al., "Ca2+ -Regulated Photoproteins: Structural Insight into the Bioluminescence Mechanism," *Acc. Chem. Res.*, 37 (6): 405-415 (2004).
Bondar et al., "Cadmium-Induced Luminescence of Recombinant Photoprotein Obelin," *Biochimica et Biophysica Acta*, 1231: 29-32 (1995).
Deng et al., "Structural Basis for the Emission of Violet Bioluminescence from a W92F Obelin Mutant," *FEBS Letters*, 506(3): 281-285 (Oct. 12, 2001).
Head et al., "The Crystal Structure of the Photoprotein Aequorin at 2.3 A Resolution," *Nature*, 405(6784): 372-376 (May 18, 2000).
Inouye et al., "Cloning and Sequence Analysis of cDNA for the Luminescent Protein Aequorin," *Proc. Natl. Acad. Sci. USA*, 82(10): 3154-3158 (May 1985).
Stephenson et al., "Studies on the Luminescent Response of the $Ca^{2+}$ -Activated Photoprotein, Obelin," *Biochimica et Biophysica Acta*, 678: 65-75 (1981).
Jena Bioscience, "Crystallization screens—JBScreen PEG/Salt, 2004," available at http://www.jenabioscience.com/index.php/5314c472c8c9389eb2e90848aba236cd/1/catalog/1005 (Retrieved Feb. 3, 2007).
The Patent Office: Patents Directorate, Search Report for Application No. GB0608514.6, dated Mar. 12, 2007.

(Continued)

*Primary Examiner*—Jon P Weber
*Assistant Examiner*—Paul C. Martin
(74) *Attorney, Agent, or Firm*—Leydig, Voit & Mayer, Ltd.

(57) ABSTRACT

Methods for enhancing luminescence of a luciferase (BFP-aq) with fluorescence activity derived from a calcium-binding photoprotein are provided. To a luciferase solution with fluorescence activity that contains an apoprotein, a calcium-binding photoprotein, which is constituted such that a coelenteramide or an analog thereof is coordinated inside, a coelenterazine that is the luminescent substrate of the luciferase or an analog thereof and a compound (e.g., imidazole etc.) having the function of removing an —NH-proton of the pyrazine ring of the imidazopyrazine skeleton in the coelenterazine or the analog thereof are added.

12 Claims, 5 Drawing Sheets

OTHER PUBLICATIONS

The Patent Office Patents Directorate, Search Report for Application No. GB0608514.6, dated Aug. 18, 2007.

Inouye, et al. "Blue Fluorescent Protein from the Calcium-Sensitive Photoprotein Aequorin: Catalytic Properties for the Oxidation of Coelenterazine as an Oxygenase," *FEBS Letters*, 580: 1977-1982 (2006).

Inouye et al., "The Use of Renilla Luciferase, Oplophorus Luciferase, and Apoaequorin as Bioluminescent Reporter Protein in the Presence of Coelenterazine Analogues as Substrate," *Biochemical and Biophysical Research Communications*, 233(2): 349-353 (Apr. 17, 1997).

Inouye, "Blue Fluorescent Protein from the Calcium-Sensitive Photoprotein Aequorin is a Heat Resistant Enzyme, Catalyzing the Oxidation of Coelenterazine," *FEBS Letters*, 577(1-2):105-110 (2004).

* cited by examiner

— Prior Art —

-- Prior Art --

— Prior Art —

SEQUENCE LISTING

<160> NUMBER OF SEQ ID NOS: 4

<210> SEQ ID NO 1
<211> LENGTH: 189
<212> TYPE: PRT
<213> ORGANISM: Aequorea aequorea

<400> SEQUENCE: 1

Val Lys Leu Thr Ser Asp Phe Asp Asn Pro Arg Trp Ile Gly Arg His
1               5                   10                  15

Lys His Met Phe Asn Phe Leu Asp Val Asn His Asn Gly Lys Ile Ser
            20                  25                  30

Leu Asp Glu Met Val Tyr Lys Ala Ser Asp Ile Val Ile Asn Asn Leu
        35                  40                  45

Gly Ala Thr Pro Glu Gln Ala Lys Arg His Lys Asp Ala Val Glu Ala
    50                  55                  60

Phe Phe Gly Gly Ala Gly Met Lys Tyr Gly Val Glu Thr Asp Trp Pro
65                  70                  75                  80

Ala Tyr Ile Glu Gly Trp Lys Lys Leu Ala Thr Asp Glu Leu Glu Lys
                85                  90                  95

Tyr Ala Lys Asn Glu Pro Thr Leu Ile Arg Ile Trp Gly Asp Ala Leu
            100                 105                 110

Phe Asp Ile Val Asp Lys Asp Gln Asn Gly Ala Ile Thr Leu Asp Glu
        115                 120                 125

Trp Lys Ala Tyr Thr Lys Ala Ala Gly Ile Ile Gln Ser Ser Glu Asp
    130                 135                 140

Cys Glu Glu Thr Phe Arg Val Cys Asp Ile Asp Glu Ser Gly Gln Leu
145                 150                 155                 160

Asp Val Asp Glu Met Thr Arg Gln His Leu Gly Phe Trp Tyr Thr Met
                165                 170                 175

Asp Pro Ala Cys Glu Lys Leu Tyr Gly Gly Ala Val Pro
            180                 185

<210> SEQ ID NO 2
<211> LENGTH: 195
<212> TYPE: PRT
<213> ORGANISM: Obelia longissima

<400> SEQUENCE: 2

Met Ser Ser Lys Tyr Ala Val Lys Leu Lys Thr Asp Phe Asp Asn Pro
1               5                   10                  15

Arg Trp Ile Lys Arg His Lys His Met Phe Asp Phe Leu Asp Ile Asn
            20                  25                  30

Gly Asn Gly Lys Ile Thr Leu Asp Glu Ile Val Ser Lys Ala Ser Asp
        35                  40                  45

Asp Ile Cys Ala Lys Leu Glu Ala Thr Pro Glu Gln Thr Lys Arg His
    50                  55                  60

Gln Val Cys Val Glu Ala Phe Phe Arg Gly Cys Gly Met Glu Tyr Gly
65                  70                  75                  80

Lys Glu Ile Ala Phe Pro Gln Phe Leu Asp Gly Trp Lys Gln Leu Ala
                85                  90                  95

Thr Ser Glu Leu Lys Lys Trp Ala Arg Asn Glu Pro Thr Leu Ile Arg
            100                 105                 110

Glu Trp Gly Asp Ala Val Phe Asp Ile Phe Asp Lys Asp Gly Ser Gly
        115                 120                 125

```
Thr Ile Thr Leu Asp Glu Trp Lys Ala Tyr Gly Lys Ile Ser Gly Ile
        130                 135                 140

Ser Pro Ser Gln Glu Asp Cys Glu Ala Thr Phe Arg His Cys Asp Leu
145                 150                 155                 160

Asp Asn Ser Gly Asp Leu Asp Val Asp Glu Met Thr Arg Gln His Leu
                165                 170                 175

Gly Phe Trp Tyr Thr Leu Asp Pro Glu Ala Asp Gly Leu Tyr Gly Asn
            180                 185                 190

Gly Val Pro
        195

<210> SEQ ID NO 3
<211> LENGTH: 198
<212> TYPE: PRT
<213> ORGANISM: Clytia gregarium

<400> SEQUENCE: 3

Met Ala Asp Thr Ala Ser Lys Tyr Ala Val Lys Leu Arg Pro Asn Phe
1               5                   10                  15

Asp Asn Pro Lys Trp Val Asn Arg His Lys Phe Met Phe Asn Phe Leu
            20                  25                  30

Asp Ile Asn Gly Asp Gly Lys Ile Thr Leu Asp Glu Ile Val Ser Lys
        35                  40                  45

Ala Ser Asp Asp Ile Cys Ala Lys Leu Gly Ala Thr Pro Glu Gln Thr
    50                  55                  60

Lys Arg His Gln Asp Ala Val Glu Ala Phe Phe Lys Lys Ile Gly Met
65                  70                  75                  80

Asp Tyr Gly Lys Glu Val Glu Phe Pro Ala Phe Val Asp Gly Trp Lys
                85                  90                  95

Glu Leu Ala Asn Tyr Asp Leu Lys Leu Trp Ser Gln Asn Lys Lys Ser
            100                 105                 110

Leu Ile Arg Asp Trp Gly Glu Ala Val Phe Asp Ile Phe Asp Lys Asp
        115                 120                 125

Gly Ser Gly Ser Ile Ser Leu Asp Glu Trp Lys Ala Tyr Gly Arg Ile
    130                 135                 140

Ser Gly Ile Cys Ser Ser Asp Glu Asp Ala Glu Lys Thr Phe Lys His
145                 150                 155                 160

Cys Asp Leu Asp Asn Ser Gly Lys Leu Asp Val Asp Glu Met Thr Arg
                165                 170                 175

Gln His Leu Gly Phe Trp Tyr Thr Leu Asp Pro Asn Ala Asp Gly Leu
            180                 185                 190

Tyr Gly Asn Phe Val Pro
        195

<210> SEQ ID NO 4
<211> LENGTH: 198
<212> TYPE: PRT
<213> ORGANISM: Mitrocoma cellularia

<400> SEQUENCE: 4

Met Ser Met Gly Ser Arg Tyr Ala Val Lys Leu Thr Thr Asp Phe Asp
1               5                   10                  15

Asn Pro Lys Trp Ile Ala Arg His Lys His Met Phe Asn Phe Leu Asp
            20                  25                  30

Ile Asn Ser Asn Gly Gln Ile Asn Leu Asn Glu Met Val His Lys Ala
        35                  40                  45
```

```
Ser Asn Ile Ile Cys Lys Lys Leu Gly Ala Thr Glu Glu Gln Thr Lys
    50                  55                  60

Arg His Gln Lys Cys Val Glu Asp Phe Phe Gly Gly Ala Gly Leu Glu
65                  70                  75                  80

Tyr Asp Lys Asp Thr Thr Trp Pro Glu Tyr Ile Glu Gly Trp Lys Arg
                85                  90                  95

Leu Ala Lys Thr Glu Leu Glu Arg His Ser Lys Asn Gln Val Thr Leu
            100                 105                 110

Ile Arg Leu Trp Gly Asp Ala Leu Phe Asp Ile Ile Asp Lys Asp Arg
        115                 120                 125

Asn Gly Ser Val Ser Leu Asp Glu Trp Ile Gln Tyr Thr His Cys Ala
    130                 135                 140

Gly Ile Gln Gln Ser Arg Gly Gln Cys Glu Ala Thr Phe Ala His Cys
145                 150                 155                 160

Asp Leu Asp Gly Asp Gly Lys Leu Asp Val Asp Glu Met Thr Arg Gln
                165                 170                 175

His Leu Gly Phe Trp Tyr Ser Val Asp Pro Thr Cys Glu Gly Leu Tyr
            180                 185                 190

Gly Gly Ala Val Pro Tyr
            195
```

METHOD FOR ENHANCING ACTIVITY OF LUCIFERASE WITH FLUORESCENCE ACTIVITY

CROSS REFERENCE TO RELATED APPLICATIONS

This application claims the benefit of priority to Japan Patent Application No. 2005-99244, filed on Mar. 30, 2005, which is incorporated herein by reference.

1. Technical Field

The present invention relates to methods for enhancing luminescence activity of a luciferase with fluorescence activity that can be used as a detection marker in biological experiments.

2. Description of the Related Art

The present inventors have been attempting to establish a method for preparing a novel protein BFP-aq from the calcium-binding photoprotein aequorin, and investigating its properties. BFP-aq exhibits not only fluorescence activity by generating fluorescence by light excitation but also luciferase activity by catalyzing oxidative luminescence by acting on a luminescent substrate (Inouye, S. (2004) FEBS Lett. 105-110).

This novel protein BFP-aq is a complex in which coelenteramide or its analog is coordinated inside the apoprotein and calcium ions etc. are bound to this apoprotein.

In general, enzymatic luminescence reaction is the oxidation reaction in which a substrate "luciferin" (a low-molecular organic compound) is oxidized by an enzyme called "luciferase" as a catalyst. As a result, when excited molecular species of oxyluciferin generated returns to the ground state, energy is released as light (photons). It has been shown that the sensitivity for detecting light (photons) generated by luciferase is 10 to 1000-fold higher than that for detecting fluorescence generated by applying excitation light on a fluorescent protein.

SUMMARY OF THE INVENTION

Since, besides having fluorescence activity, BFP-aq has the above-described luciferase luminescence activity and further has heat resistance that no other luciferase possesses, it has a great utility value in a wide variety of fields in industry. Therefore, by enhancing the activities, more highly sensitive detection methods can be provided and its range of application can also be expected to become wider.

In view of the above-mentioned object, the present invention aims at providing methods for enhancing luminescence of a luciferase BFP-aq with fluorescence activity derived from a calcium-binding photoprotein.

The inventors focused attention on the mechanism of light-emitting reaction of coelenterazine in order to enhance the luminous efficiency of BFP-aq. That is, they have examined and assiduously studied the mechanism like the electronic theory of organic chemistry in the light-emitting reaction using the natural luminescent substrate coelenterazine or its derivative as substrate, and, as a result, found how to solve the problem described above by using the following constitutions. The present invention has thus been accomplished. The present invention encompasses the following:

1. A method for enhancing luminescence of a luciferase with fluorescence activity that contains an apoprotein in which a coelenteramide or its analog is coordinated, which includes adding to a solution of the luciferase with the fluorescence activity a coelenterazine that is a luminescent substrate of the luciferase or its analog and a compound having the function of removing an —NH— proton of the pyrazine ring of the imidazopyrazine skeleton in the coelenterazine or the analog thereof.

2. The method according to 1, wherein the compound having the proton-removing function is imidazole.

3. The method according to 1 or 2, wherein the luciferase contains an apoprotein of a calcium-binding photoprotein, a coelenteramide or its analog, and a calcium ion or a divalent or trivalent ion that can be substituted for the calcium ion, and wherein, in a molecule of the luciferase, the ratio of the number of molecules of the apoprotein to the number of molecules of the coelenteramide or the analog thereof is 1:1 and the ratio of the number of molecules of the apoprotein to the number of molecules of the calcium ion or the divalent or trivalent ion that can be substituted for the calcium ion is 1:1 to 1:4.

4. The method according to any one of 1 to 3, wherein the apoprotein is a protein selected from the group consisting of apoaequorin, apoclytin, apoobelin, apomitrocomin, apomineopsin, and apobervoin.

5. The method according to any one of 1 to 4, wherein the luciferase with fluorescence activity contains an apoprotein having the amino acid sequence shown in SEQ ID NOs: 1 to 4 or a mutant apoprotein in which one or more amino acids are deleted, substituted, or added in the sequence shown in SEQ ID NOs: 1 to 4.

6. The method according to any one of 1 to 5,
wherein the coelenteramide or the analog thereof is represented by the following formula (1) or (2):

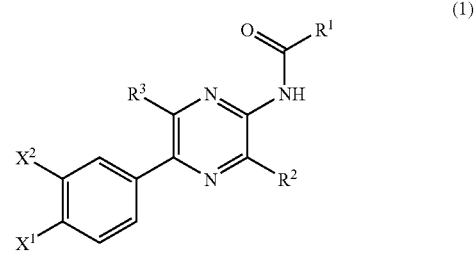

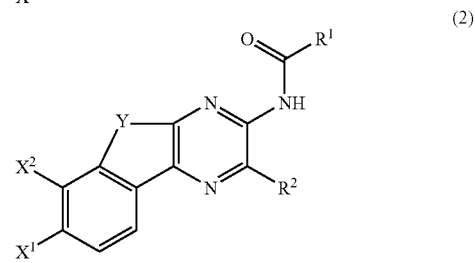

wherein $R^1$ is a substituted or unsubstituted aryl group, a substituted or unsubstituted arylated alkyl group, or a straight or branched chain alkyl group that may be substituted by an aliphatic cyclic group;

$R^2$ is a substituted or unsubstituted aryl group, a substituted or unsubstituted arylated alkyl group, a substituted or unsubstituted aryl alkenyl group, a straight or branched chain alkyl group that may be substituted by an aliphatic cyclic group, a straight or branched chain alkenyl group that may be substituted by an aliphatic cyclic group, or a heterocyclic group;

R³ is a hydrogen atom, or a substituted or unsubstituted alkyl group;

X¹ is a hydrogen atom, a hydroxyl group, a halogen atom, an alkoxyl group, or an amino group;

X² is a hydrogen atom or a hydroxyl group; and

Y is a divalent hydrocarbon group having 1 to 4 carbon atoms.

7. The method according to 6, wherein, in the formula (1) or (2),

R¹ is an unsubstituted aryl group, an unsubstituted arylated alkyl group, an arylated alkyl group substituted by a hydroxyl group or a halogen atom, or a straight or branched chain alkyl group that may be substituted by a cyclohexyl group;

R² is an unsubstituted aryl group, an aryl group substituted by a hydroxyl group, an unsubstituted arylated alkyl group, an arylated alkyl group substituted by a hydroxyl group, an unsubstituted aryl alkenyl group, an unsubstituted straight or branched chain alkyl group, a straight chain alkyl group that may be substituted by an aliphatic cyclic group, a branched chain alkenyl group, or a heterocyclic group containing sulfur;

R³ is a hydrogen atom, a methyl group, or 2-hydroxyethyl group;

X¹ is a hydrogen atom, a hydroxyl group, a fluorine atom, a methoxy group, or an amino group; and Y is a methylene group, an ethylene group, a propylene group, or a vinylene group.

8. The method according to 7, wherein, in the formula (1) or (2),

R¹ is a phenyl group, a benzyl group, a p-hydroxybenzyl group, a p-fluorobenzyl group, a p-chlorobenzyl group, a p-bromobenzyl group, a p-iodinebenzyl group, a 3, 4-difluorobenzyl group, a pentafluorobenzyl group, a phenylethyl group, a phenylpropyl group, a naphthylmethyl group, a cyclohexylmethyl group, a methyl group, a 1-methylpropyl group, or a 2-methylpropyl group; and R² is a phenyl group, a p-hydroxy phenyl group, a benzyl group, an α-hydroxybenzyl group, a phenylethyl group, a phenylvinyl group, a cyclohexyl group, a cyclohexylmethyl group, a cyclohexylethyl group, a methyl group, an ethyl group, a propyl group, a 2-methylpropyl group, a 2-methylpropenyl group, an adamantylmethyl group, a cyclopentylmethyl group, or a thiophene-2-yl group.

9. The method according to any one of 1 to 8, wherein the coelenterazine or the analog thereof is represented in the following formula (3) or (4):

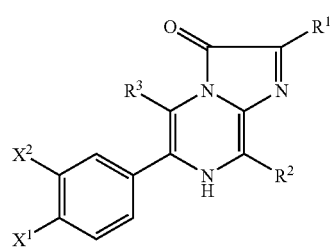

(3)

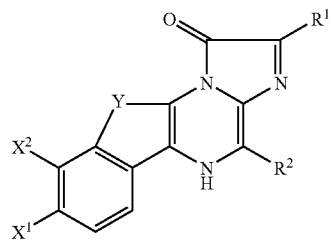

(4)

wherein

R¹ is a substituted or unsubstituted aryl group, a substituted or unsubstituted arylated alkyl group, or a straight or branched chain alkyl group that may be substituted by an aliphatic cyclic group;

R² is a substituted or unsubstituted aryl group, a substituted or unsubstituted arylated alkyl group, a substituted or unsubstituted aryl alkenyl group, a straight or branched chain alkyl group that may be substituted by an aliphatic cyclic group, a straight or branched chain alkenyl group that may be substituted by an aliphatic cyclic group, or a heterocyclic group;

R³ is a hydrogen atom, or a substituted or unsubstituted alkyl group;

X¹ is a hydrogen atom, a hydroxyl group, a halogen atom, an alkoxyl group, or an amino group;

X² is a hydrogen atom or a hydroxyl group; and

Y is a divalent hydrocarbon group having 1 to 4 carbon atoms.

10. The method according to 9, wherein, in the formula (3) or formula (4),

R¹ is an unsubstituted aryl group, an unsubstituted arylated alkyl group, an arylated alkyl group substituted by a hydroxyl group or a halogen atom, or a straight or branched chain alkyl group that may be substituted by a cyclohexyl group;

R² is an unsubstituted aryl group, an aryl group substituted by a hydroxyl group, an unsubstituted arylated alkyl group, an arylated alkyl group substituted with a hydroxyl group, an unsubstituted aryl alkenyl group, an unsubstituted straight or branched chain alkyl group, a straight chain alkyl group that may be substituted by an aliphatic cyclic group, a branched chain alkenyl group, or a heterocyclic group containing sulfur;

R³ is a hydrogen atom, a methyl group, or 2-hydroxyethyl group;

X¹ is a hydrogen atom, a hydroxyl group, a fluorine atom, a methoxy group, or an amino group; and Y is a methylene group, ethylene group, a propylene group, or a vinylene group.

11. The method according to 10, wherein, in the formula (3) or (4),

R¹ is a phenyl group, a benzyl group , a p-hydroxybenzyl group, a p-fluorobenzyl group, a p-chlorobenzyl group, a p-bromobenzyl group, a p-iodinebenzyl group, a 3, 4-difluorobenzyl group, a pentafluorobenzyl group, a phenylethyl group, a phenylpropyl group, a naphthylmethyl group, a cyclohexylmethyl group, a methyl group, a 1-methylpropyl group, or a 2-methylpropyl group;

and R² is a phenyl group, a p-hydroxy phenyl group, a benzyl group, an α-hydroxybenzyl group, a phenylethyl group, a phenylvinyl group, a cyclohexyl group, a cyclohexylmethyl group, a cyclohexylethyl group, a methyl group, an ethyl group, a propyl group, a 2-methylpropyl group, a 2-methylpropenyl group, an adamantylmethyl group, a cyclopentylmethyl group, or a thiophene-2-yl group.

12. The method according to any one of 1 to 8, wherein the analog of the coelenterazine is at least a compound selected from a group consisting of h-coelenterazine, f-coelenterazine, cp-coelenterazine, and hcp-coelenterazine.

13. Use of a compound having the function of removing an —NH— proton of the pyrazine ring of the imidazopyrazine skeleton in a coelenterazine or its analog for preparing a luminescence-enhancing agent for enhancing light emission generated from a luciferase with a fluorescence activity that contains an apoprotein in which a coelenteramide or its analog is coordinated.

14. Use of a compound according to 13, wherein the compound having the proton-removing function is imidazole.

15. A kit containing:
a luciferase with fluorescence activity that contains an apoprotein in which a coelenteramide or its analog is coordinated;
a coelenterazine that is the luminescent substrate of the luciferase or its analog; and
a luminescence-enhancing agent that can enhance light emission of the luciferase,
wherein the luminescence-enhancing agent is a compound having the function of removing an —NH— proton of the pyrazine ring of the imidazopyrazine skeleton in the coelenterazine or its analog.

16. The kit according to 15, wherein the compound having the proton-removing function is imidazole.

17. A method for enhancing luminescence of a BFP-aq that contains an apoaequorin in which a coelenteramide is coordinated, including adding a hcp-coelenterazine and imidazole to a solution of the BFP-aq.

DESCRIPTION OF THE PREFERRED EMBODIMENT

Figure 1:
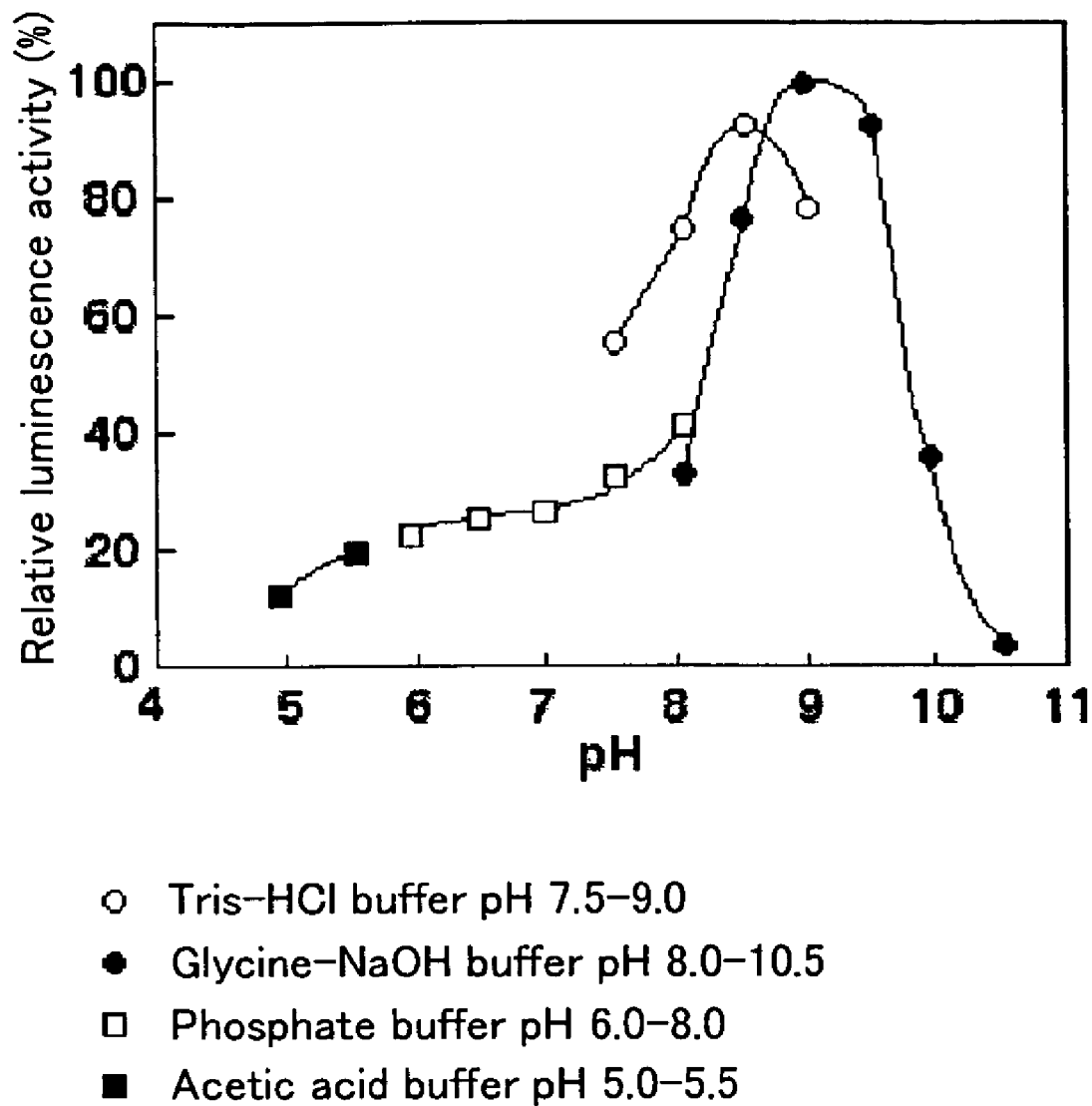
FIG. 1 shows relative luminescence activities of the luciferase with fluorescence activity (BFP-aq) at pHs indicated in the Example according to the present invention.

The present invention is directed to methods for enhancing the luminescence activity of a luciferase (BFP-aq) with fluorescence activity derived from a calcium-binding photoprotein by adding to a solution of BFP-aq a compound having the function of removing an NH proton of the pyrazine ring of the imidazopyrazine skeleton in the substrate coelenterazine and its analog.

==Luciferase (BFP-aq) with Fluorescence Activity==

1. Composition and Structure of a Luciferase (BFP-aq) with Fluorescence Activity The luciferase (BFP-aq) with fluorescence activity, which has chemiluminescence activity, to be used for the present invention is composed of the apoprotein of a calcium-binding photoprotein, coelenteramide or its analog, and calcium ions or divalent or trivalent ions that can be substituted for the calcium ions. In the complex of apoprotein and coelenteramide or its analog, the ratio of the number of molecules of the apoprotein to that of the coelenteramide or its analog is preferably 1:1. In the complex of apoprotein and calcium ions or divalent or trivalent ions that can be substituted for the calcium ions, the ratio of the number of molecules of the apoprotein to that of the calcium ions or divalent or trivalent ions is preferably 1:1 to 1:4, more preferably 1:2 to 1:3, most preferably 1:3. In this BFP-aq, coelenteramide or its analog is coordinated inside the apoprotein, and calcium ions are bound mainly to the EF-hands of the apoprotein.

Having an excellent thermal stability as compared with other luciferases, this BFP-aq is applicable to the fields in which luciferase could never be used.

2. Production of a Luciferase (BFP-aq) with Chemiluminescence Activity

BFP-aq can be produced by reacting a calcium-binding photoprotein with calcium ions or divalent or trivalent ions that can be substituted by calcium ions under an extremely gentle (i.e., extremely slow in reaction velocity) condition. "Reacting under a gentle condition" in the present invention refers to reacting under conditions such that after a calcium-binding photoprotein is reacted with calcium ions etc., coelenteramide or its analog remains coordinated to the apoprotein and disulfide bonds are not substantially formed.

Such reaction conditions include, for example, overlaying a highly viscous solution of a calcium-binding photoprotein with an extremely thin solution of calcium ions etc. and reacting them at low temperature for a long time. In this case, the reaction temperature is preferably 0 to 30° C., more preferably 4° C. The reaction time is preferably 24 hours or longer, though it varies depending on the concentration of the protein.

In the reaction, the concentration of calcium ions is preferably lower. This is because the lower the concentration of calcium ions the less frequently calcium ions contact (react) with a calcium-binding photoprotein. On the contrary, the concentration of a calcium-binding photoprotein solution is preferably higher. This is because the higher the concentration of a protein solution the higher the viscosity of the protein complex solution and the more slowly the mixing of the calcium ion solution and the protein complex solution proceeds.

Specifically, an aqueous solution of calcium ions or divalent or trivalent ions that can be substituted for the calcium ions at a concentration of $10^{-7}$ M (mol/l) or lower is added so that its molar ratio to a calcium ion-binding photoprotein is 1 to 4. The molar ratio of ions, such as calcium ions, to a calcium-binding photoprotein may be equal to or greater than the ratio of the number of molecules (e.g., 4 or greater) in the luciferase (BFP-aq) with fluorescence activity of interest, as long as the reaction proceeds slowly. To attain reaction conditions required for the present invention, modifications such as change of reaction vessel design, use of different solvents, and use of a semipermeable membrane are possible, and the descriptions herein should not be construed as limitations on the scope of the invention.

3. Apoprotein that Constitutes a Luciferase (BFP-aq) with Fluorescence Activity

The apoprotein of a calcium-binding photoprotein is used as an apoprotein that constitutes BFP-aq. "A calcium-binding photoprotein" as used herein refers to a protein that reacts with calcium ions or divalent or trivalent ions equivalent thereto and emits light. The examples of the calcium-binding photoprotein include aequorin, clytin, obelin, mitrocomin, mineopsin, and bervoin. They may be either prepared from natural organisms or produced by genetic engineering. In addition, the amino acid sequence of the calcium-binding photoprotein may be mutated by gene recombination technology, as long as it has the aforementioned luminescence activity.

Table 1 lists the calcium ion-binding photoproteins whose gene has been isolated to date.

TABLE 1

| Name of photoprotein | Scientific name | Japanese name/ Common name | GenBank Acc. No | Authors (year) |
|---|---|---|---|---|
| Aequorin | *Aequorea victoria* | Owankurage | AEVAQ440X: L29571 | Inouye et al. (1985) |
| Aequorin | *Aequorea victoria* | Owankurage | — | Charbonnueau et al.(1985) |
| Aequorin | *Aequorea victoria* | Owankurage | AEVAEQA: M16103 | Prasher et al. (1987) |
| Aequorin | *Aequorea parva* | Owankurage | AY013822 | Luo et al. (2000) |
| Aequorin | *Aequorea macrodactyla* | Hitomoshikurage | AY013823 | Luo et al. (2000) |
| Clytin | *Clytia gregarium* | Kozarakurage | CY1APOCLYT: L13247 | Inouye & Tsuji(1993) |
| Mitrocomin | *Mitrocoma cellularia* | | MITMI17: L31623 | Fagan et al. (1993) |
| Obelin | *Obelia longissima* | Oberiakurage | OLU07128: U07128 | Illarionov et al. (1995) |
| Obelin | *Obelia geniculata* | Oberiakurage | AF394688 | Markova et al. (2002) |

The homology of the amino acid sequences of these apoproteins is 60% or higher, and all of these apoproteins can be regenerated to calcium-binding photoproteins from the luminescent substrate coelenterazine. Further, recent x-ray crystal analysis of aequorin and obelin, both of which are photoproteins, has revealed that the backbone structures of their higher-order structures are almost the same. From this, homology of the higher-order structures of other calcium-binding photoproteins can easily be inferred by analogy. Thus, although aequorin, a typical calcium-binding photoprotein, was used in Examples herein, the results obtained can be obviously applicable to other calcium-binding photoproteins.

The amino acid sequence of the apoaequorin that is the apoprotein of natural aequorin is shown in SEQ ID NO: 1 in the sequence listing. Besides the apoaequorin having amino acid sequence described in SEQ ID NO: 1, any apoaequorin mutant can be used whether it may be known or unknown as long as it is capable of constituting a calcium-binding photoprotein. The apoaequorin used in the present invention thus includes the apoaequorin having the amino acid sequence described in SEQ ID NO: 1 as well as mutant apoaequorins in which one or more amino acids are deleted, substituted, or added in the amino acid sequence described n SEQ ID NO: 1. One example of a particularly preferred mutant apoaequorin is the mutant in which the first Val is substituted with Ala-Asn-Ser in SEQ ID NO: 1.

The amino acid sequence of the apoclytin that is the apoprotein of the wild-type clytin, is shown in SEQ ID NO: 2 in the sequence listing. The amino acid sequence of the apoobelin that is the apoprotein of the wild-type obelin, is shown in SEQ ID NO: 3 in the sequence listing. The amino acid sequence of the apomitrocomin that is the apoprotein of the wild-type mitrocomin, is shown in SEQ ID NO: 4 in the sequence listing. These may be mutants in which one or more amino acids are deleted, substituted, or added in each of the sequences.

BFP-aq loses its chemiluminescence activity when the free sulfhydryl groups of cysteine residues in the apoprotein are oxidized to form a disulfide bond. Therefore it is considered that mutated apoproteins, in which free sulfhydryl groups are deleted or substituted, whereby a disulfide bond cannot be formed, never lose its chemiluminescence activity. For example, it is expected that a fluorescent protein that has a serine residue in place of its cysteine residue sustains its activity because the disulfide bonds cannot be formed.

4. Coelenteramide that Constitutes a Luciferase (BFP-aq) with Fluorescence Activity The coelenteramide or its analog is represented by the following formula (1) or (2):

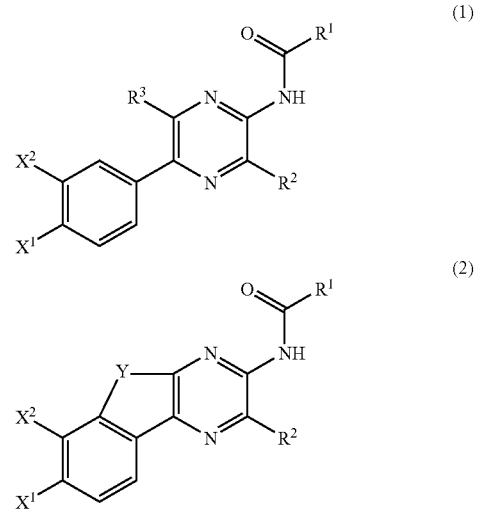

$R^1$ is a substituted or unsubstituted aryl group, a substituted or unsubstituted arylated alkyl group, or a straight or branched chain alkyl group that may be substituted by an aliphatic cyclic group, preferably an unsubstituted aryl group, an unsubstituted arylated alkyl group, arylated alkyl group that substitued by an hydroxyl group or halogen atom, or a straight or branched chain alkyl group that may be substituted by a cyclohexyl group, more preferably a phenyl group, a benzyl group, a p-hydroxybenzyl group, a p-fluorobenzyl group, a p-chlorobenzyl group, a p-bromobenzyl group, a p-iodinebenzyl group, a 3,4-difluorobenzyl group, a pentafluorobenzyl group, a phenylethyl group, a phenylpropyl group, a naphthylmethyl group, a. cyclohexylmethyl group, a methyl group, a 1-methylpropyl group, or a 2-methylpropyl group;

$R^2$ is a substituted or unsubstituted aryl group, a substituted or unsubstituted arylated alkyl group, a substituted or unsubstituted aryl alkenyl group, a straight or branched chain alkyl group that may be substituted by an aliphatic cyclic group, a straight or branched chain alkenyl group that may be substituted by an aliphatic cyclic group, or a heterocyclic group, preferably an unsubstituted aryl group, aryl group that substitued by an hydroxyl group, an unsubstituted arylated alkyl group, arylated alkyl group that substitued by an hydroxyl group, an unsubstituted aryl alkenyl group, a straight or branched chain alkyl group, an unsubstituted straight or branched chain alkyl group, a straight chain alkyl group that may be substituted by an aliphatic cyclic group, a branched chain alkenyl group, or a sulfurous heterocyclic group, more preferably a phenyl group, a p-hydroxy phenyl group, a benzyl group, an α-hydroxybenzyl group, a phenylethyl group, a phenylvinyl group, a cyclohexyl group, a cyclohexylmethyl group, a cyclohexylethyl group, a methyl group, an ethyl group, a propyl group, a 2-methylpropyl group, a 2-methylpropenyl group, an adamantylmethyl group, a cyclopentylmethyl group, or a thiophene-2-yl group;

$R^3$ is a hydrogen atom, a substituted or unsubstituted alkyl group, preferably a hydrogen atom, a methyl group, or 2-hydroxyethyl group;

$X^1$ is a hydrogen atom, a hydroxyl group, a halogen atom, an alkoxyl group, or an amino group, particularly preferably a hydrogen atom, a hydroxyl group, a fluorine atom, a methoxy group, or an amino group;

$X^2$ is a hydrogen atom or a hydroxyl group; and

Y is a divalent hydrocarbon group having 1 to 4 carbon atoms, preferably a methylene group, ethylene group, a propylene group, or a vinylene group.

5. Luciferase with Fluorescence Activity Uses Coelenterazine as a Luminescent Substrate.

The coelenterazine or its analog is represented by the following formula (3) or (4):

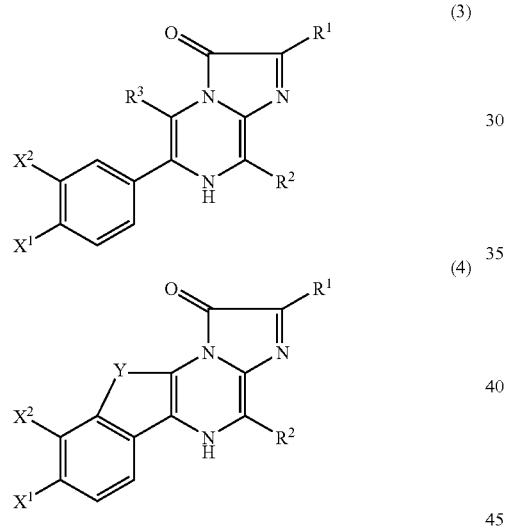

wherein $R^1$, $R^2$, $R^3$, $X^1$, $X^2$, and Y are identical to those in formula (1) or (2).

In the present invention, coelenterazine and its analogs, h-coelenterazine, f-coelenterazine, cp-coelenterazine, and hcp-coelenterazine, can be particularly preferably used as luminescence substrates.

The chemical structural formulae of these compounds and coelenteramide are collectively shown below.

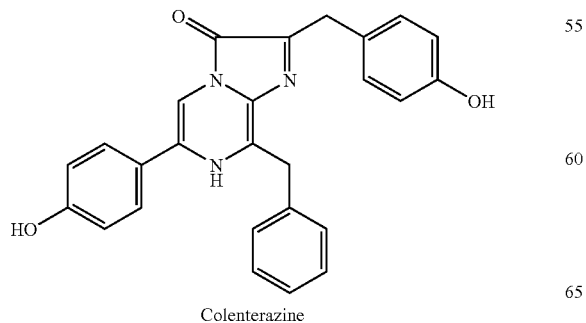

Colenterazine

-continued

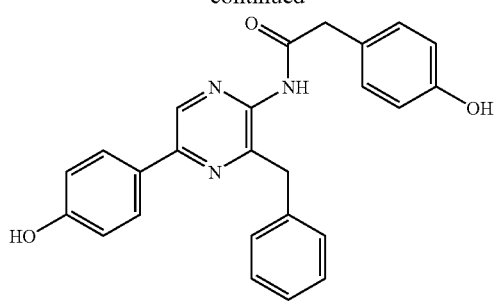

Coelenteramide

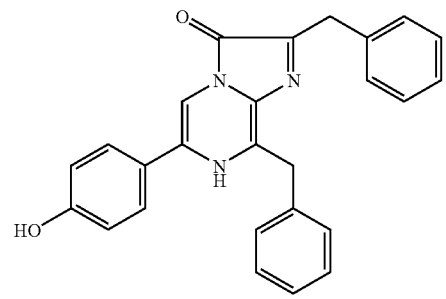

h-Coelenterazine

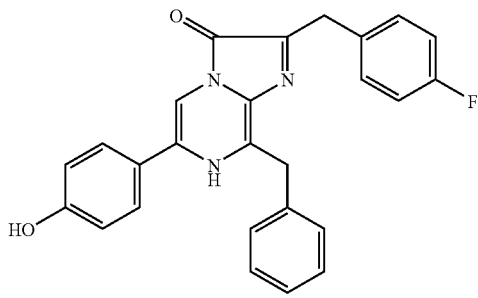

f-Coelenterazine

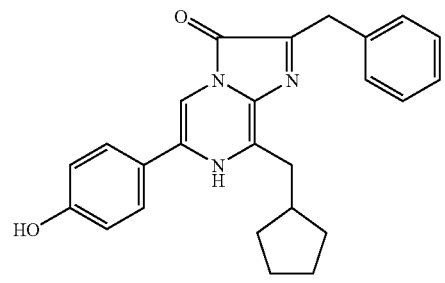

hcp-Coelenterazine

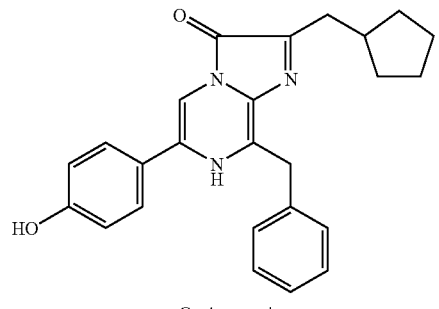

cp-Coelenterazine

6. Metal Ions that Constitute Luciferase (BFP-aq) with fluorescence activity Metal ions that bind to BFP-aq are calcium ions or divalent or trivalent ions that can be substituted for the calcium ions. "Ions that can be substituted for the calcium ions" as used herein refers to those ions which cause a light-emitting reaction when they react with a calcium-binding photoprotein such as aequorin in place of calcium ions. In other words, they refer to ions that exert the similar function to calcium ions on a calcium-binding photoprotein. Examples of such ions include magnesium ions ($Mg^{2+}$), strontium ions ($SR^{2+}$), barium ions ($Ba^{2+}$), lead ions ($Pb^{2+}$), cobalt ions ($Co^{2+}$), nickel ions ($Ni^{2+}$) cadmium ions ($Cd^{2+}$), yttrium ions ($Y^{3+}$), lanthanum ions ($La^{3+}$), samarium ions ($Sm^{3+}$), europium ions ($Eu^{3+}$), dysprosium ions ($Dy^{3+}$), thulium ions ($Tm^{3+}$), and yttribium ions ($Yb^{3+}$). Among these, divalent metal ions are preferable and divalent ions of metals other than transition metals (e.g., $Ca^{2+}$, $SR^{2+}$, and $Pb^{2+}$) are more preferable.

In addition, binding of one molecule of these ions to the so-called EF-hand of a calcium-binding photoprotein molecule is sufficient, but binding of two or more molecules is preferable and binding of three molecules is particularly preferable.

Table 2 lists typical luciferases using coelenterazine as substrate.

concentration of the luminescence-enhancing agent can be 30 to 350 mM, preferably 60 to 300 mM.

For easy use, this luminescence-enhancing agent may be provided as a kit together with a luciferase (BFP-aq) with fluorescence activity, coelenterazine or its analog.

EXAMPLE

The present invention is explained in the following examples, but these examples are not to be construed to limit the present invention.

==Preparation of Recombinant Apoaequorin==

To obtain recombinant apoaequorins, the apoaequorin gene expression vector piP-HE (Japanese Laid-Open Application No. 1989-132397) constructed from pAQ440 harboring the apoaequorin gene (Japanese Laid-Open Application No. 1986-135586) was used. The recombinant apoaequorins encoded by piP-HE is composed of 191 amino acids, whose N-terminus starts from Ala-Asn-Ser-(Val of the N-terminus of SEQ ID NO: 1 in the sequence listing was replaced by Ala-Asn-Ser-).

The above-mentioned expression vector piP-HE was introduced into *E. coli* strain WA802 using the conventional meth-

TABLE 2

Luciferases using coelenterazine as substrate

| Name of luciferase | Scientific name | Japanese name/ Common name | GenBank Acc. No | Authors (year) |
|---|---|---|---|---|
| *Renilla* | *Renilla reniformis* | Umishiitake (*Renilla reniformis*) | RELLUC: M63501 | Lorenz et al.(1991) |
| *Renilla* | *Renilla muelleri* | Umishiitake (*Renilla reniformis*) | AY015988 | Bryan & S.-Gyorgyi (1999) |
| Copepoda | *Gaussia princeps* | Gaussia princes | AY015993 | Bryan & S.-Gyorgyi (1999) |
| Copepoda | *Pleuromamma* sp. | Pleuromamma | AY015994 | Bryan & S.-Gyorgyi (1999) |
| Copepoda | *Metridia longa* | Metridia | AX452573 | Golz et al.(2002) |
| Decapoda | *Oplophorus gracilorostris* | Himehiodoshiebi (*Oplophorus gracilorostris*) | AB030245, AB030246 | Inouye et al.(2000) |

==Method for Enhancing Luminescence of BFP-aq==

A light-emitting reaction that uses natural coelenterazine as luminescent substrate is performed using a luciferase (BFP-aq) with fluorescence activity prepared as mentioned above. In this reaction, a compound for removing —NH— protons from the imidazopyrazine skeleton of coelenterazine, i.e., a compound that can serve as a proton acceptor, is added as a luminescence-enhancing agent.

Any compound can be used as a luminescence-enhancing agent as long as it has the above-mentioned function. Examples of such compounds commonly and easily available include imidazole, histamine, L-histidine, 2-methylimidazole, 4-methylimidazole, urocanic acid, 5-amino-4-imidazole-carboxyamide, L-arginine, acetamide, guanidine, L-lysine, urea, triethylamine, etc., among which imidazole in particular can be preferably used. In addition, these compounds can be used alone or in combination of two or more. Further, since this light-emitting reaction is preferably performed in a water system, a water-soluble luminescence-enhancing agent is preferred.

The reaction condition is not particularly limited, but around pH 8.0 is preferred, at which fluorescence activity of BFP-aq is stable and luciferase activity is high enough. Further, by taking into account the optimum pH of the light-emitting reaction of BFP-aq and pKa of the compound added, the strength of the function of removing an —NH— proton can be predicted. A luminescence-enhancing agent can therefore be appropreately selected depending on the use. The ods. The transformant obtained was incubated on the agar medium containing ampicillin (50 μg/(ml)) at 30° C. overnight, inoculated into 50 ml of LB liquid medium (bactotrypton 1% w/v, yeast extract 0.5% w/v, sodium chloride 0.5% w/v, pH 7.2 in water) containing ampicillin (50 μg/ml), and incubated at 30° C. for 8 hours. Then, the culture was added to 2 L of a fresh LB liquid media and incubated at 37° C. for a day and a night(18 hours) After incubation, the resulting culture was separated into bacterial cells and medium by low-speed centrifugation (5,000×g). Since both the bacterial cells and the medium contain expressed recombinant apoaequorins, they were stored separately as the starting material for aequorin purification.

First, the recombinant apoaequorins were recovered from the bacterial cells. The harvested bacterial cells were suspended in 400 ml of buffer (50 mM Tris-HCl, pH 7.6, 10 mM EDTA) containing 200 mg of a reducing agent dithiothreitol (DTT, manufactured by Wako Pure Chemicals Industries, Ltd.). The cells were crushed by treating with an ultrasonicator for 2 min on ice and centrifuged at 12,000×g for 20 min and then the supernatant was recovered. Chemosynthesized coelenterazine (a solution in ethanol) was added to the supernatant obtained at 1.2-fold molar concentration of apoaequorin to be produced, and allowed to stand at 4° C. for more than 5 hours.

This supernatant was immediately loaded onto a Q-SEPHAROSE™ column (Amersham Pharmacia Biotech, 2×10 cm diameter) pre-equilibrated with a buffer of TE (20 mM Tris-HCl, pH 7.6, 10 mM EDTA) to have aequorin adsorbed. The column was washed with TEN (20 mM Tris-HCl, pH 7.6, 10 mM EDTA, 0.1 M NaCl) until the absorbance of the solution from the column at 280 nm becomes 0.05 or less. Then, the apoaequorin and aequorin fractions adsorbed on the column were eluted with a linear concentration gradient of 0.1 to 0.4 M-NaCl.

Regenerated aequorin was isolated from unregenerated apoaequorin, using a hydrophobic chromatography with Butyl SEPHAROSE 4 Fast Flow gel. That is, the orange eluate from the Q-SEPHAROSE column was adjusted at final ammonium sulfate concentration of 2 M, and then the precipitant was removed by centrifugation. The supernatant was applied to a Butyl SEPHAROSE 4 Fast Flow column (Amersham Pharmacia Biotech, column size: 2×8 cm diameter) pre-equilibrated with TE containing 2 M ammonium sulfate and the orange regenerated aequorin fractions having chemiluminescence activity were eluted by a linear concentration gradient to a final ammonium sulfate concentration at 1 M and recovered. On the other hand, the unregenerated apoaequorin was eluted in TE.

The regenerated aequorin fractions were analyzed by SDS-PAGE using 12% polyacrylamide gel under a reducing condition. As a result, a single band with a molecular weight equivalent to that of a 25 kDa protein was detected in the purified fractions, with a purity of 98% or higher according to densitometer measurement. The recovery rate of aequorin from the bacterial cells was about 80%. A total of 80 mg of high-purity aequorin was obtained.

Meanwhile, high-purity aequorin was purified from the culture medium according to the method described in Japanese Laid-Open Application No. 1989-132397. That is, the culture medium was subjected to acidification treatment to pH 5 or below and allowed to stand at 40° C. for 60 mm or longer. The white-precipitated apoaequorin was isolated by centrifugation and dissolved in the above-mentioned buffer (50 mM Tris-HCl, pH 7.6, 10 mM EDTA) containing a reducing agent. Then, after regenerating to aequorin in the same manner as in purification method from bacterial cells, aequorin was purified by the SEPHAROSE column chromatography and the Butyl SEPHAROSE 4 Fast Flow column chromatography. The resulting purified aequorin was analyzed by SDS-PAGE using 12% polyacrylamide gel under a reducing condition. As a result, a single band with a molecular weight equivalent to that of a 25 kDa protein was detected with a purity of 98% or higher according to densitometer measurement. A total of 45 mg of high-purity aequorin was obtained from 50 mg of apoaequorin obtained from the culture medium. The amount of proteins was determined using a commercially available kit (manufactured by Bio-Rad Laboratories, Inc.) based on the Bradford method. Bovine serum albumin (manufactured by Pierce Laboratories Inc.) was used as the standard substance.

==Preparation of Luciferase (BFP-aq) with Fluorescence Activity==

An aequorin solution with an aequorin concentration of 8 mg/ml was prepared by dissolving the purified aequorin described in Example 1 in a buffer containing 10 mM Tris-HCl (pH 7.6), 2 mM EDTA, and 1.2 M ammonium sulfate.

An aequorin solution with an aequorin concentration of 8 mg/ml was prepared by dissolving the purified aequorin described in Example 1 in a buffer containing 10 mM Tris-HCl (pH 7.6), 2 mM EDTA, and 1.2 M ammonium sulfate. 1 ml of this aequorin solution was centrifuged at 5000×g at 40° C. for 60 min or longer with a high speed refrigerated centrifuge (CR20B2; manufactured by Hitachi Ltd.), using a VIVASPIN 2 column (Manufactured by Zartorius K.K.) with a high-speed ultrafiltration filter, a polyethersulfone membrane with a fraction molecular weight of 10,000. The solution was concentrated to a total quantity of 0.1 ml or smaller. Further, to lower the EDTA concentration of the concentrated solution to 0.1 μM or lower, 1 ml of 10 μM Tris-HCl containing 0.1 μM EDTA was added to the VIVASPIN 2 column, which was centrifuged under the same condition. This concentration process was repeated at least two times. The resulting concentrated aequorin solution looked yellow-red, which could be confirmed easily by the naked eye.

BFP-aq was prepared in the following procedures. In a VIVASPIN 2 column, the concentrated aequorin solution was overlaid with 0.9 ml of 50 mM Tris-HCl (pH 7.6) containing 5 mM calcium chloride (Wako Pure Chemicals Industries, Ltd.) and 2 mM dithiothreitol (Wako Pure Chemicals Industries, Ltd.) to trigger continuous light emission and the column was allowed to stand at 40° C. for 24 hours or longer. The end of the light-emitting reaction could also be confirmed by disappearance of the yellow-red color from the aequorin solution. Further, 2 ml of 50 mM Tris-HCl (pH 7.6) containing 5 mM calcium chloride (Wako Pure Chemicals Industries, Ltd.) and 2 mM dithiothreitol (Wako Pure Chemicals Industries, Ltd.) was loaded onto the VIVASPIN 2 column and the column was centrifuged under the identical conditions and then washed. Generated BFP-aq was confirmed to emit blue fluorescence under a long wavelength UV lamp (maximum wavelength: 366 nm).

==Method for Preparing Recombinant *Renilla reniformis* Luciferase==

*Renilla reniformis* luciferase, a monomeric luciferase (36 kDa) derived from *Renilla reniformis*, catalyzes oxidation of the substrate coelenterazine to trigger light emission. Here, *Renilla reniformis* luciferase was used for a control (experiment) as an example of the luciferase that does not have fluorescence activity.

To express *Renilla reniformis* luciferase in *E. coli*, the expression vector pHis-RLase containing a recombinant gene with a histidine tag at its N-terminus, which encodes *Renilla reniformis* luciferase was used.

This expression vector pHis-RLase was prepared based on the known method (Biochem. Biophys. Res. Commun. 233, 349-353). The expression vector pHis-RLase was introduced into *E. coli* Top10 using the conventional method. The transformant obtained was pre-cultured in 10 ml of LB liquid medium (bactotrypton 1% w/v, yeast extract 0.5% w/v, sodium chloride 0.5% w/v, pH 7.2 in water) containing ampicillin (50 μg/ml) at 24° C. for a day and a night(18 hours), and then cultured in 400 ml of LB liquid medium at 36° C. for 2 hours. Then, isopropyl β-D(-)-thiogalactopyranoside (IPTG, manufactured by Wako Pure Chemical Industries, Ltd.) was added to the liquid medium at a final concentration of 0.2 mM, and the transformant was further incubated at the same temperature for 3 hours. Then, the bacterial cells were recovered by centrifugation (5,000 rpm×5 min, 3,000×g) to be used as the starting material for purification of the recombinant *Renilla reniformis* luciferase.

The harvested bacterial cells were suspended in 5 ml of 50 mM Tris-HCl (pH 7.6) and ultrasonicated (on a Branson sonifier, Model cycle 250) twice for 3min on ice. The bacterial cell lysate was centrifuged at 12,000 rpm (17,700×g) for 20 min and the supernatant was recovered. Then, the supernatant was loaded onto a nickel chelate column (Amersham Biosciences, column size: diameter 1.5×5 cm ) to have Renilla reniformis luciferase adsorbed. The *Renilla reniformis* luciferase adsorbed was eluted with 0.5 M imidazole (manufactured by Wako Pure Chemical Industries, Ltd.) and the resulting *Renilla reniformis* luciferase active fractions were dialyzed against 5 L of 0.1 M ammonium carbonate solution (pH 8.0) at 4° C. overnight.

The *Renilla reniformis* luciferase active fractions dialyzed were again adsorbed to a nickel chelate column (Amersham Biosciences, column size:diameter 1.5×5 cm ), eluted with a linear concentration gradient at imidazole concentrations ranging between 0 and 0.3 M to obtain further purified *Renilla reniformis* luciferase active fractions. The *Renilla reniformis* luciferase was eluted at imidazole concentrations between 0.12 and 0.13 M.

Next, the resulting *Renilla reniformis* luciferase fractions were loaded onto a Q-SEPHAROSE column (Amersham Biosciences, column size: diameter 2.5×5 cm) to have them adsorbed, and eluted with a linear concentration gradient of 20 mM Tris-HCl (pH 7.6) containing 5 mM EDTA at sodium chloride concentrations ranging between 0 and 0.4 M to obtain further purified *Renilla reniformis* luciferase active fractions. *Renilla reniformis* luciferase was eluted at sodium chloride concentrations between 0.2 to 0.22 M; the purity was confirmed to be 95% or higher by 12% SDS-polyacrylamide electrophoresis.

==Method for Measuring Luminescence Activity using *Renilla reniformis* Luciferase==

50 mM Tris-HCl buffer (200 µl), pH 7.6, was pre-warmed at 25° C., to which the substrate coelenterazine (1 µg/µl) dissolved in ethanol was added. A light-emitting reaction was triggered by adding *Renilla reniformis* luciferase (1.2 µg). Luminescence activity was measured with the luminometer Luminescencer-PSN AB2200 (manufactured by Atto Co., Ltd.) for 60 seconds. The measured values were represented as the maximum intensity (Imax) of luminescence activity.

==Examination of Optimum pH of Light-Emitting Reaction of BFP-aq==

50 mM Tris-HCl buffers (200 µl), pH 7.6 to 10.5, were pre-warmed at 25° C., to which the substrate coelenterazine (1 µg) was then added. A light-emitting reaction was triggered by adding BFP-aq (1.2 µg). Luminescence activity was measured with the luminometer Luminescencer-PSN AB2200 (manufactured by Atto Co., Ltd.) for 60 seconds. Assuming that the maximum intensity activity (Imax) of BFP-aq luminescence activity in 50 mM Tris-HCl (pH 8.0) is 100%, the relative luminescence activity values at each pH are shown in FIG. 1.

==Enhancing Effect of BFP-aq on the Luminescence by Addition of Organic Compounds==

Figure 2:
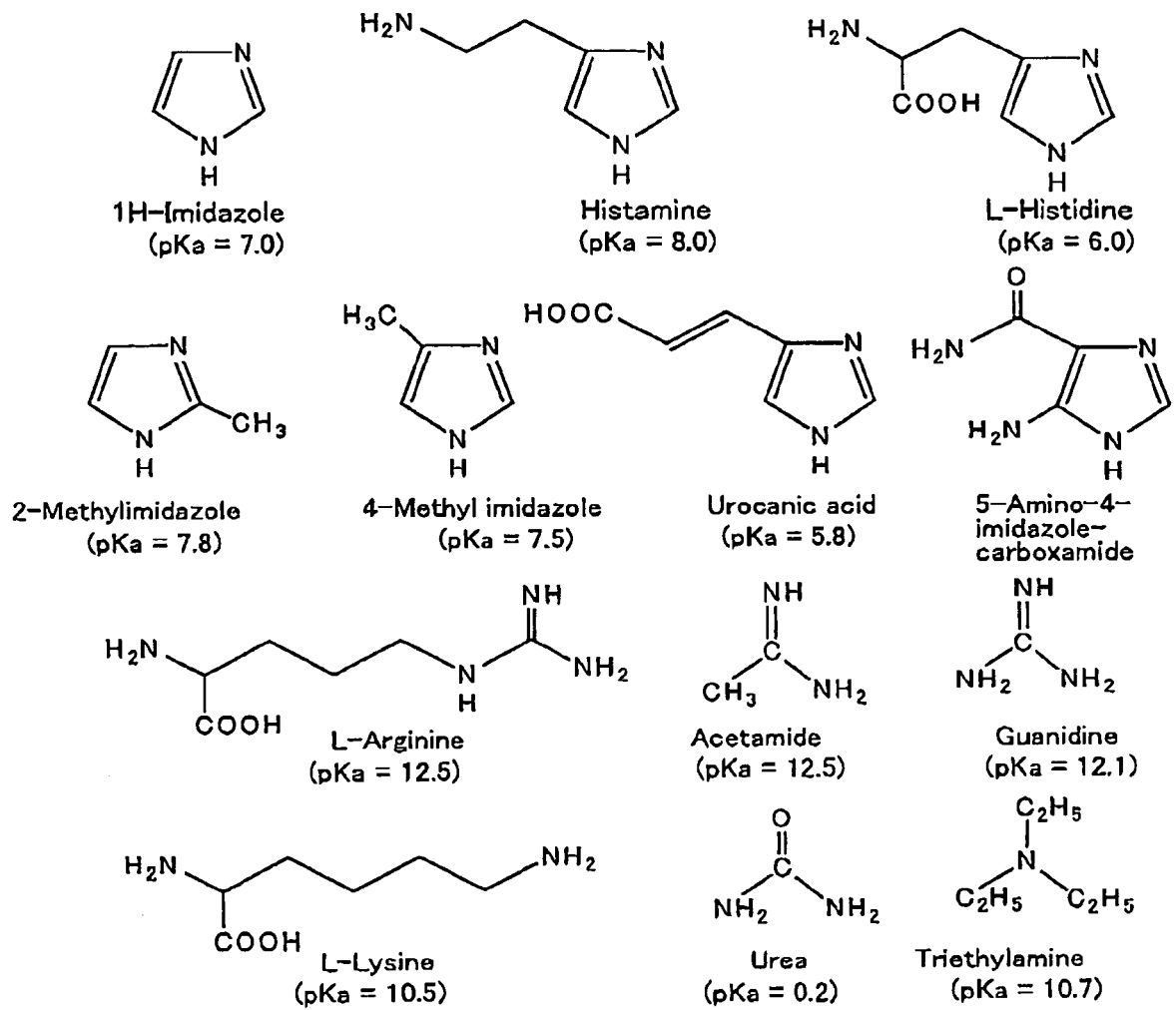
FIG. 2 shows the structural formulae of the compounds used for search of organic compounds that enhance the activity of the luciferase with fluorescence activity in Example according to the present invention.

Solutions of 50 mM Tris-HCl (pH 8.0), each containing various commercial organic compounds shown in Table 3, were prepared and pre-warmed at 25° C. The substrate coelenterazine (1 µg) was added to the solutions (200 µl) containing each of these compounds. After further addition of BFP-aq (1.2 µg), the mixture was stirred. Then, luminescence activity was measured with the luminometer Luminescencer-PSN AB2200 (manufactured by Atto Co., Ltd.) for 60 seconds. Assuming that the maximum intensity activity (Imax) of BFP-aq luminescence activity in 50 mM Tris-HCl (pH 8.0) is 100%, the relative luminescence activity values are shown in Table 4. In addition, the structural formula of each organic compound is shown in FIG. 2.

TABLE 3

Compounds used for search of organic compounds to enhance activation of luciferase with fluorescence activity

| Name of compound | Name of selling company | Product number |
| --- | --- | --- |
| Imidazole | Wako Pure Chemical Industries, Ltd. | 091-00012 |
| 2-Methylimidazole | Wako Pure Chemical Industries, Ltd. | 138-11162 |
| 4-Methylimidazole | Wako Pure Chemical Industries, Ltd. | 132-11202 |
| Histamine | Wako Pure Chemical Industries, Ltd. | 084-00643 |
| Urocanic acid | Tokyo Chemical Industry Co., Ltd. | I0002 |

TABLE 3-continued

Compounds used for search of organic compounds to enhance activation of luciferase with fluorescence activity

| Name of compound | Name of selling company | Product number |
| --- | --- | --- |
| 5-Amino-imidazole-4-carboxamide/hydrochloride | Sigma | A8004 |
| L-Histidine | Wako Pure Chemical Industries, Ltd. | 084-00682 |
| L-Arginine | Wako Pure Chemical Industries, Ltd. | 017-04612 |
| L-Lysine | Sigma | L5501 |
| L-Glycine | Wako Pure Chemical Industries, Ltd. | 077-00735 |
| L-Alanine | Wako Pure Chemical Industries, Ltd. | 010-01042 |
| Guanidine/hydrochloride | Wako Pure Chemical Industries, Ltd. | 077-02435 |
| Urea | Wako Pure Chemical Industries, Ltd. | 217-00171 |
| Acetamide/hydrochloride | Wako Pure Chemical Industries, Ltd. | 014-14791 |
| Triethylammonium hydrogen carbonate | Nacalai Tesque | 348-35 |

TABLE 4

Activation of BFP-aq luminescence activity by addition of organic compounds

| Compound | pKa | Concentration (mM) | Luminescence activity (%) Imax | Luminescence activity (%) Initial velocity |
| --- | --- | --- | --- | --- |
| None | — | — | 100 | 100 |
| (Imidazole compounds) | | | | |
| Imidazole | 7.0 | 30 | 148 | 153 |
|  |  | 150 | 199 | 205 |
| 2-Methylimidazole | 7.8 | 30 | 63 | 83 |
|  |  | 150 | 16 | 21 |
| 4-Methylimidazole | 7.5 | 30 | 88 | 92 |
|  |  | 150 | 78 | 95 |
| Histamine | 8.0 | 30 | 69 | 92 |
|  |  | 150 | 22 | 26 |
| L-Histidine | 6.0 | 30 | 37 | 82 |
|  |  | 150 | 5 | 27 |
| Urocanic acid | 5.8 | 30 | 44 | 31 |
|  |  | 150[a] | — | — |
| 5-Amino-imidazole-4-carboxyamide/hydrochlorid |  | 30 | 64 | 48 |
|  |  | 150 | 0 | 2 |
| (Guanidyl compounds) | | | | |
| L-Arginine | 12.5 | 30 | 62 | 73 |
|  |  | 150 | 1 | 4 |
| Guanidine/hydrochloride | 12.1 | 30 | 92 | 130 |
|  |  | 150 | 109 | 226 |
|  |  | 300 | 65 | 118 |
| Acetamide/hydrochloride | 12.5 | 30 | 73 | 132 |
|  |  | 150 | 31 | 44 |
|  |  | 300 | 55 | 95 |
| (Other compounds) | | | | |
| Urea | 0.2 | 30 | 84 | 113 |
|  |  | 150 | 89 | 104 |
|  |  | 3000 | 29 | 57 |
| Triethylamine | 10.7 | 30 | 68 | 68 |
|  |  | 150 | 8 | 12 |
| L-Lysine | 10.5 | 30 | 60 | 66 |
|  |  | 150 | 1 | 10 |
| L-Glycine | 6.0 | 30 | 87 | 104 |
|  |  | 150 | 83 | 78 |
| L-Alanine | 6.0 | 30 | 88 | 82 |
|  |  | 150 | 77 | 59 |

[a]Not dissolved

Figure 3:
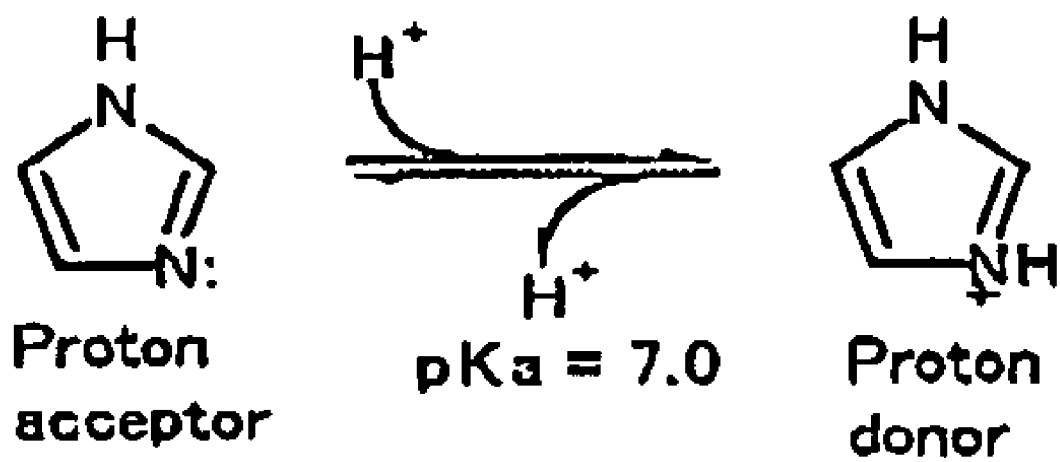
FIG. 3 shows protonation of imidazole.
Figure 4:
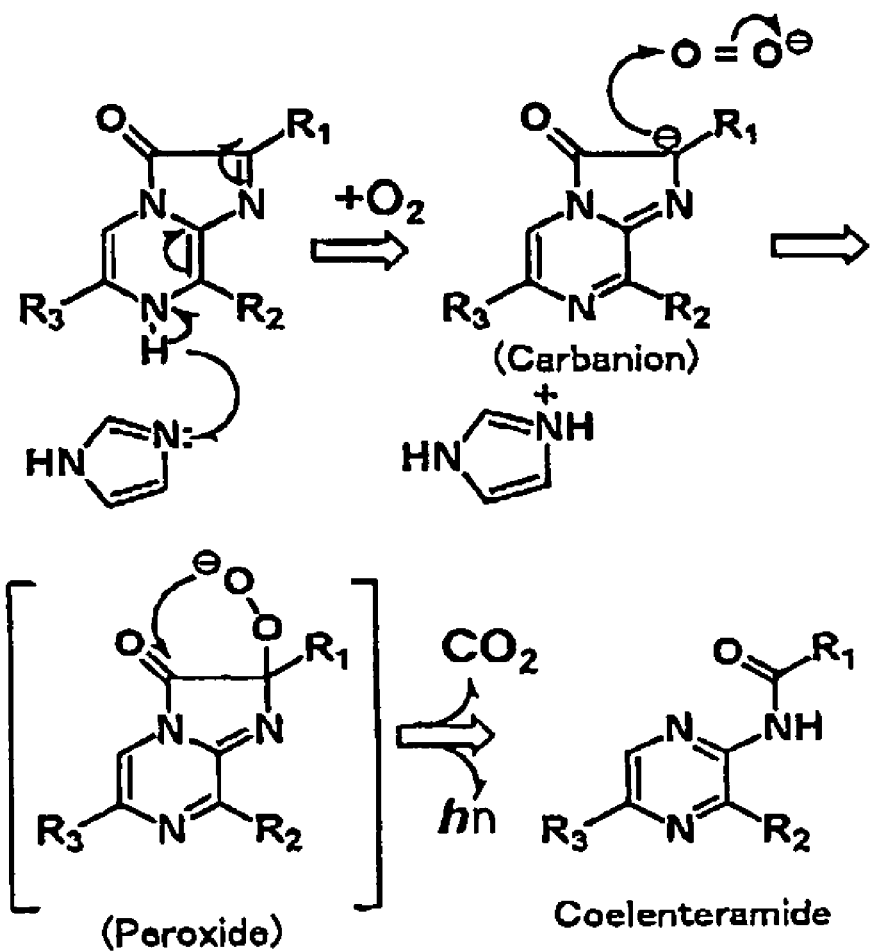
FIG. 4 shows the mechanism by which imidazole enhances the activity of the luciferase with fluorescence activity.

Comparison of the relative luminescence activity values in Table 4 reveals that a marked luminescence activity (Imax) occurs only when 150 mM imidazole was added to the light-emitting reaction system. The reason was considered to be due to the following mechanism: Considering that pKa of imidazole is 7.0, imidazole readily acts as a proton acceptor under alkaline conditions, as shown in FIG. 3. In a light-emitting reaction at pH 8.0, as shown in FIG. 4, imidazole acts as an acceptor of the proton at position 7 of the substrate coelenterazine and enhances the removal of the proton, thereby promoting oxygenation to coelenterazine and making a light-emitting reaction proceed efficiently.

In contrast, luminescence activity was not enhanced in other compounds. This indicates that, at pH 8.0, none of these compounds act as an acceptor of the proton at position 7 of coelenterazine. This is probably because, besides pKa, either the effect of the side chain of imidazole or the physical risk due to the molecular size prevents the compounds from acting on coelenterazine within BFP-aq.

==Determination of Optimal Concentrations for the Enhancing Effect of BFP-aq on Luminescence by Addition of Imidazole==

Figure 5:
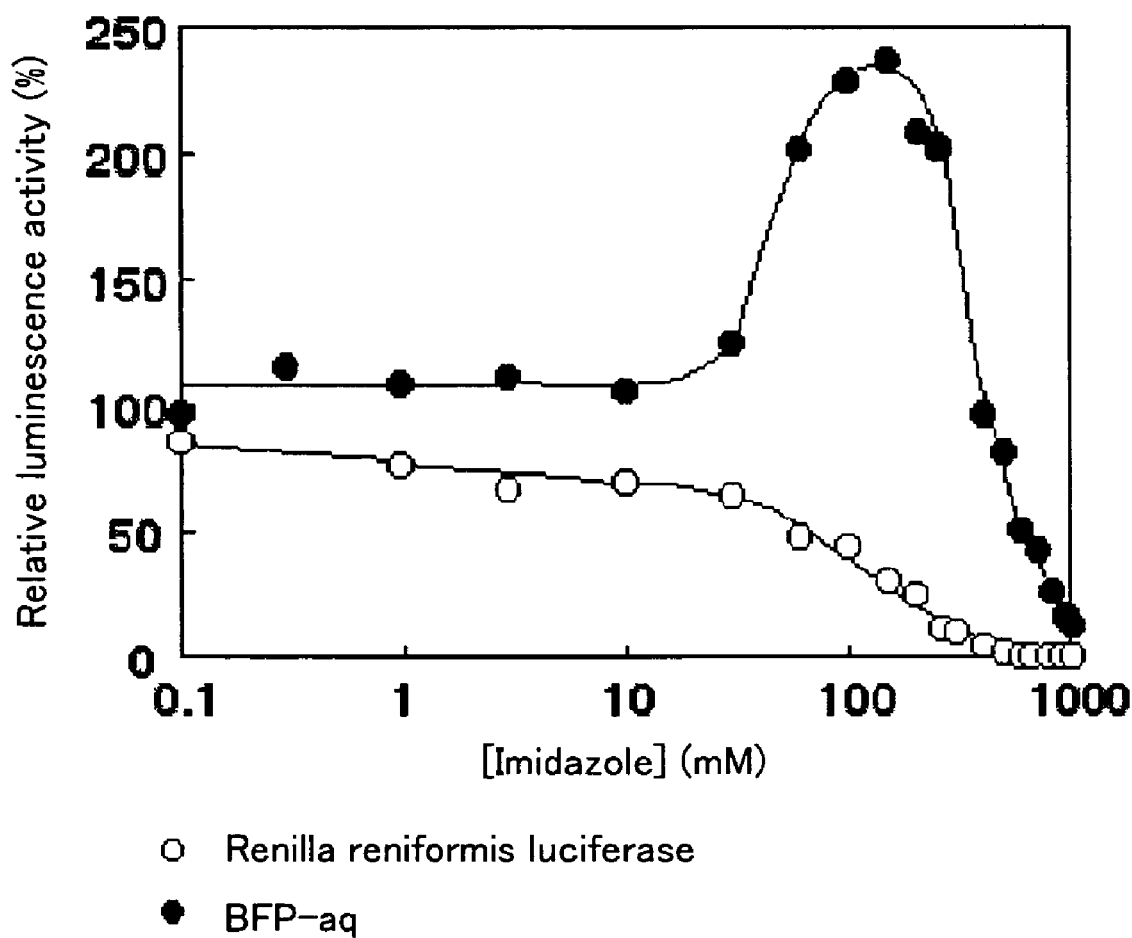
FIG. 5 shows the relative luminescence activities of the luciferase with fluorescence activity and Renilla reniformis luciferase by the addition of imidazole at concentrations indicated in the Example according to the present invention.

50 mM Tris-HCl (pH 8.0) containing imidazole at various concentrations (0. 1, 0.3, 1, 3, 10, 30, 60, 100, 150, 200, 250, 300, 400, 500, 600, 700, 800, 900, and 1000 mM) was prepared and pre-warmed at 25° C. The substrate coelenterazine (1 µg) was added to each imidazole-containing solution (200 µl). After further addition of BFP-aq (1.2 µg), the mixture was stirred. Then, luminescence activity was measured with the luminometer Luminescencer-PSN AB2200 (manufactured by Atto Co., Ltd.) for 60 seconds. Assuming that the maximum intensity activity (Imax) of BFP-aq luminescence activity in 50 mM Tris-HCl (pH 8.0) is 100%, the relative luminescence activity values are shown in FIG. 5.

As a control experiment, the same experiment was conducted using *Renilla reniformis* luciferase, which contains coelenterazine as luminescent substrate. The results revealed that the luminescence activity of *Renilla reniformis* luciferase is remarkably inhibited with increasing concentrations of imidazole, whereas the luminescence activity of BFP-aq is enhanced at 30 to 250 mM imidazole. Especially by adding 150 mM imidazole, more than two-fold of the luminescence activity can be obtained, compared with the system without the addition of imidazole. That is, it was shown that the enhancing effect on luminescence activity by the addition of imidazole is specific for BFP-aq.

==Method for Enhancing Luminescence Activity by Combination of a Coelenterazine Analog and BFP-aq with the Addition of Imidazole==

50 mM Tris-HCl (pH 8.0) containing 150 mM imidazole was prepared and pre-warmed at 25° C. 200 µl of this solution was placed in five vessels, to each of which 1 µg of the substrate coelenterazine (CTZ) and its four analogs: h-CTZ, cp-CTZ, hcp-CTZ, f-CTZ were added. After further addition of BFP-aq (1.2 µg), the mixture was stirred. Then, luminescence activity was measured with the luminometer Luminescencer-PSN AB2200 (manufactured by Atto Co., Ltd.) for 60 seconds. Assuming that the maximum intensity activity (Imax) and initial velocity of BFP-aq luminescence activity in 50 mM Tris-HCl (pH 8.0) was 100%, the effect of the addition of imidazole on luminescence activity was examined.

TABLE 5

Relative luminescence activity by combination of a coelenterazine analog and BFP-aq with the addition of imidazole

| | Relative luminescence activity | | | |
|---|---|---|---|---|
| | Imax (%) | | Initial velocity (%) | |
| Coelenterazine and its analog | Without imidazole | With imidazole | Without imidazole | With imidazole |
| Coelenterazine | 100[a] | 199 | 100[b] | 322 |
| h-Coelenterazine | 123 | 280 | 154 | 525 |
| hcp-Coelenterazine | 279 | 375 | 1144 | 2766 |
| cp-Coelenterazine | 54 | 138 | 152 | 535 |
| f-Coelenterazine | 130 | 203 | 96 | 332 |

[a] $3.1 \times 10^5$ Relative luminescence value
[b] $3.1 \times 10^4$ Relative luminescence value/sec Comparison of relative luminescence activity values specific to each coelenterazine substrate shown in Table 5 indicates that, in the BFP-aq light-emitting reaction system, h-coelenterazine, f-coelenterazine, cp-coelenterazine, and hcp-coelenterazine served as effective substrates. Further, the examination of the effect of the addition of imidazole on luminescence activity showed that when hcp-coelenterazine was used as substrate with the addition of 150 mM imidazole, Imax 10 was 4-fold higher and the velocity of a light-emitting reaction was 25-fold higher than those obtained when coelenterazine is used without the addition of imidazole. That is, it was shown that luminescence of BFP-aq can be enhanced by the addition of a coelenterazine analog and imidazole.

==Determination of the Light-Emitting Reaction Rate of BFP-aq by Addition of Imidazole==

Coelenterazine was added at various concentrations to 200 µl of 50 mM Tris-HCl (pH 8.0) containing 150 mM imidazole at final concentration of 1.2 to 11.8 µM and the mixture was pre-warmed at 25° C. After further addition of BFP-aq (1.2 µg), the mixture was stirred. Then, luminescence activity was measured with the luminometer Luminescencer-PSN AB2200 (manufactured by Atto Co., Ltd.) for 60 seconds. Using the luminescence activity for the first 3 sec of the light-emitting reaction as the initial reaction rate, Km values were determined by the Lineweaver-Burk plot method.

As a result, it was shown that no marked changes were found in the Km values in the reaction system with or without 150 mM imidazole, whereas only Vmax was doubled in the system with imidazole. That is, it was suggested that enhancement of luminescence activity by the presence of imidazole does not influence the binding between the substrate and BFP-aq but is involved in promotion to the formation process of the peroxide portion of coelenterazine or stabilization of coelenterazine carbanions.

TABLE 6

Light-emitting reaction velocity of BFP-aq with/without imidazole

| Substrate | Km value | Vmax |
|---|---|---|
| Without imidazole | 9.6 µM | 617284 rlu |
| With imidazole | 9.2 µM | 1262626 rlu |

What is claimed is:

1. A method for enhancing luminescence of a luciferase with fluorescence activity that contains an apoprotein in which a coelenteramide or an analog thereof is coordinated, comprising adding a compound selected from the group consisting of imidazole and Guanidine-HCl to a solution of the luciferase with the fluorescence activity and a coelenterazine or analog thereof and that is a luminescent substrate of the luciferase.

2. The method of claim 1, wherein the compound is imidazole.

3. The method of claim 1, wherein the luciferase comprises an apoprotein of a calcium-binding photoprotein, a coelenteramide or an analog thereof, and a calcium ion or a divalent or trivalent ion that can be substituted for the calcium ion, and wherein, in a molecule of the luciferase, the ratio of the number of molecules of the apoprotein to the number of molecules of the coelenteramide or the analog thereof is 1:1 and the ratio of the number of molecules of the apoprotein to the number of molecules of the calcium ion or the divalent or trivalent ion that can be substituted for the calcium ion is 1:1 to 1:4.

4. The method of claim 1, wherein the apoprotein is a protein selected from the group consisting of apoaequorin, apoclytin, apoobelin, apomitrocomin, apomineopsin, and apobervoin.

5. The method of claim 1, wherein the luciferase with fluorescence activity comprises an apoprotein having the amino acid sequence shown in SEQ ID NO: 1 to 4.

6. The method of a claim 1, wherein the coelenteramide or the analog thereof is represented by the following formula (1) or (2):

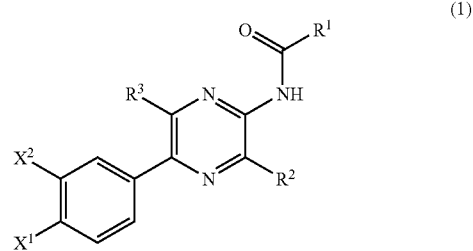

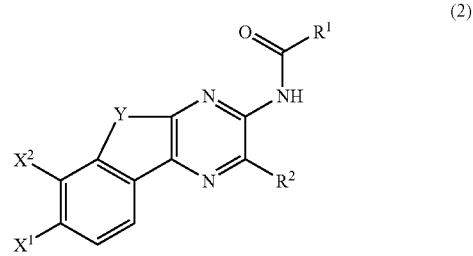

wherein $R^1$ is a substituted or unsubstituted aryl group, a substituted or unsubstituted arylated alkyl group, or a straight or branched chain alkyl group that may be substituted by an aliphatic cyclic group;

$R^2$ is a substituted or unsubstituted aryl group, a substituted or unsubstituted arylated alkyl group, a substituted or unsubstituted aryl alkenyl group, a straight or branched chain alkyl group that may be substituted by an aliphatic cyclic group, a straight or branched chain alkenyl group that may be substituted by an aliphatic cyclic group, or a heterocyclic group;

$R^3$ is a hydrogen atom, or a substituted or unsubstituted alkyl group;

$X^1$ is a hydrogen atom, a hydroxyl group, a halogen atom, an alkoxyl group, or an amino group;

$X^2$ is a hydrogen atom or a hydroxyl group; and

Y is a divalent hydrocarbon group having 1 to 4 carbon atoms.

7. The method of claim 6,
wherein, in the formula (1) or (2),
$R^1$ is an unsubstituted aryl group, an unsubstituted arylated alkyl group, an arylated alkyl group substituted by a hydroxyl group or a halogen atom, or a straight or branched chain alkyl group that may be substituted by a cyclohexyl group;
$R^2$ is an unsubstituted aryl group, an aryl group substituted by a hydroxyl group, an unsubstituted arylated alkyl group, an arylated alkyl group substituted by a hydroxyl group, an unsubstituted aryl alkenyl group, an unsubstituted straight or branched chain alkyl group, a straight chain alkyl group that may be substituted by an aliphatic cyclic group, a branched chain alkenyl group, or a heterocyclic group containing sulfur;
$R^3$ is a hydrogen atom, a methyl group, or 2-hydroxyethyl group;
$X^1$ is a hydrogen atom, a hydroxyl group, a fluorine atom, a methoxy group, or an amino group; and
Y is a methylene group, an ethylene group, a propylene group, or a vinylene group.

8. The method of claim 7, wherein, in the formula (1) or (2),
$R^1$ is a phenyl group, a benzyl group, a p-hydroxybenzyl group, a p-fluorobenzyl group, a p-chlorobenzyl group, a p-bromobenzyl group, a p-iodinebenzyl group, a 3, 4-difluorobenzyl group, a pentafluorobenzyl group, a phenylethyl group, a phenylpropyl group, a naphthylmethyl group, a cyclohexylmethyl group, a methyl group, a 1-methylpropyl group, or a 2-methylpropyl group; and
$R^2$ is a phenyl group, a p-hydroxy phenyl group, a benzyl group, an α-hydroxybenzyl group, a phenylethyl group, a phenylvinyl group, a cyclohexyl group, a cyclohexylmethyl group, a cyclohexylethyl group, a methyl group, an ethyl group, a propyl group, a 2-methylpropyl group, a 2-methylpropenyl group, an adamantylmethyl group, a cyclopentylmethyl group, or a thiophene-2-yl group.

9. The method of claim 1, wherein the coelenterazine or the analog thereof is represented in the following formula (3) or (4):

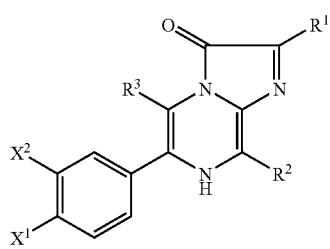

(3)

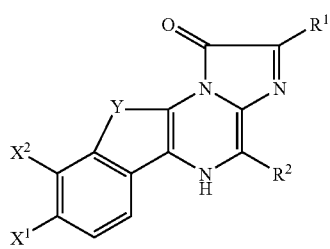

(4)

wherein
$R^1$ is a substituted or unsubstituted aryl group, a substituted or unsubstituted arylated alkyl group, or a straight or branched chain alkyl group that may be substituted by an aliphatic cyclic group;
$R^2$ is a substituted or unsubstituted aryl group, a substituted or unsubstituted arylated alkyl group, a substituted or unsubstituted aryl alkenyl group, a straight or branched chain alkyl group that may be substituted by an aliphatic cyclic group, a straight or branched chain alkenyl group that may be substituted by an aliphatic cyclic group, or a heterocyclic group;
$R^3$ is a hydrogen atom, or a substituted or unsubstituted alkyl group;
$X^1$ is a hydrogen atom, a hydroxyl group, a halogen atom, an alkoxyl group, or an amino group;
$X^2$ is a hydrogen atom or a hydroxyl group; and
Y is a divalent hydrocarbon group having 1 to 4 carbon atoms.

10. The method of claim 9, wherein, in the formula (3) or formula (4),
$R^1$ is an unsubstituted aryl group, an unsubstituted arylated alkyl group, an arylated alkyl group substituted by a hydroxyl group or a halogen atom, or a straight or branched chain alkyl group that may be substituted by a cyclohexyl group;
$R^2$ is an unsubstituted aryl group, an aryl group substituted by a hydroxyl group, an unsubstituted arylated alkyl group, an arylated alkyl group substituted with a hydroxyl group, an unsubstituted aryl alkenyl group, an unsubstituted straight or branched chain alkyl group, a straight chain alkyl group that may be substituted by an aliphatic cyclic group, a branched chain alkenyl group, or a heterocyclic group containing sulfur;
$R^3$ is a hydrogen atom, a methyl group, or 2-hydroxyethyl group;
$X^1$ is a hydrogen atom, a hydroxyl group, a fluorine atom, a methoxy group, or an amino group; and
Y is a methylene group, ethylene group, a propylene group, or a vinylene group.

11. The method of claim 10, wherein, in the formula (3) or (4),
$R^1$ is a phenyl group, a benzyl group, a p-hydroxybenzyl group, a p-fluorobenzyl group, a p-chlorobenzyl group, a p-bromobenzyl group, a p-iodinebenzyl group, a 3, 4-difluorobenzyl group, a pentafluorobenzyl group, a phenylethyl group, a phenylpropyl group, a naphthylmethyl group, a cyclohexylmethyl group, a methyl group, a 1-methylpropyl group, or a 2-methylpropyl group;
and $R^2$ is a phenyl group, a p-hydroxy phenyl group, a benzyl group, an α-hydroxybenzyl group, a phenylethyl group, a phenylvinyl group, a cyclohexyl group, a cyclohexylmethyl group, a cyclohexylethyl group, a methyl group, an ethyl group, a propyl group, a 2-methylpropyl group, a 2-methylpropenyl group, an adamantylmethyl group, a cyclopentylmethyl group, or a thiophene-2-yl group.

12. The method of claim 1, wherein the analog of the coelenterazine is at least a compound selected from a group consisting of h-coelenterazine, f-coelenterazine, cp-coelenterazine, and hcp-coelenterazine.

* * * * *